US011205255B2

(12) United States Patent
Koester et al.

(10) Patent No.: US 11,205,255 B2
(45) Date of Patent: Dec. 21, 2021

(54) GENERATING A MIXED IMAGE DATA RECORD (71) Applicant: Siemens Healthcare GmbH, Erlangen (DE)

(72) Inventors: Niko Koester, Neunkirchen am Brand (DE); Martin Hupfer, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 122 days.

(21) Appl. No.: 16/580,100

(22) Filed: Sep. 24, 2019

(65) Prior Publication Data
US 2020/0104985 A1 Apr. 2, 2020

(30) Foreign Application Priority Data
Sep. 28, 2018 (EP) ..................................... 18197539

(51) Int. Cl.
G06T 5/00 (2006.01)
G06T 5/50 (2006.01)
G06T 7/00 (2017.01)
G16H 40/67 (2018.01)
A61B 6/00 (2006.01)
G06T 5/20 (2006.01)

(52) U.S. Cl.
CPC ................ *G06T 5/50* (2013.01); *A61B 6/482* (2013.01); *G06T 5/20* (2013.01); *G06T 7/97* (2017.01); *G16H 40/67* (2018.01); *G06T 2207/10116* (2013.01); *G06T 2207/20221* (2013.01)

(58) Field of Classification Search
CPC .... G06T 5/50; G06T 5/20; G06T 7/97; G06T 2207/10116; G06T 2207/20221; G16H 40/67; A61B 6/67
See application file for complete search history.

(56) References Cited

U.S. PATENT DOCUMENTS 10,719,925 B2 * 7/2020 Lee ..................... A61B 6/482
2016/0350910 A1 * 12/2016 Jeong ..................... G06K 9/52

FOREIGN PATENT DOCUMENTS

| DE | 102009032441 A1 | 1/2011 | |
| WO | WO 0228154 A1 | 4/2002 | |
| WO | WO-2012015285 A2 * | 2/2012 | ............. A61B 6/463 |
| WO | WO 2012015285 A2 | 2/2012 | |

OTHER PUBLICATIONS

NPL: Extended European Search Report for EP Application Patent No. 18197539, dated Aug. 4, 2019.

* cited by examiner

*Primary Examiner* — Khai M Nguyen
(74) *Attorney, Agent, or Firm* — Harness, Dickey & Pierce, P.L.C.

(57) ABSTRACT

A method is for generating a mixed image data record based on energy-resolved recording via an energy-resolving X-ray detector. In an embodiment, the method includes generating a first image value of a first image element of a first image data record in a first energy range and generating a second image value of the first image element of a second image data record in a second energy range; and mixing the first image value generated and the second image value generated in dependence on an image parameter, to generate the mixed image data record with a mixed image value of the first image element.

14 Claims, 1 Drawing Sheet

GENERATING A MIXED IMAGE DATA RECORD

PRIORITY STATEMENT

The present application hereby claims priority under 35 U.S.C. § 119 to European patent application number DE 181917539.2 filed Sep. 28, 2018, the entire contents of which are hereby incorporated herein by reference.

FIELD

Embodiments of the invention generally relate to a method for generating a mixed image data record based on energy-resolved recording via an energy-resolving X-ray detector and an image-generating unit for this purpose.

BACKGROUND

Energy-resolving, in particular counting direct-conversion, X-ray detectors or integrated, in particular indirect-conversion, X-ray detectors can be used in the field of X-ray imaging, for example in computed tomography, angiography or radiography.

In direct-conversion X-ray detectors, the X-rays or photons can be converted into electrical pulses by way of a suitable converter material. The converter material used can, for example, be CdTe, CdZnTe (CZT), CdZnTeSe, CdTeSe, CdMnTe, InP, $TlBr_2$, $HgI_2$, GaAs or other materials. The electric pulses are evaluated by an electronic evaluation system, for example an integrated circuit (application specific integrated circuit, ASIC). In counting X-ray detectors, incident X-rays are measured by counting the electric pulses triggered by the absorption of X-ray photons in the converter material. In particular after a preamplifier and a shaper, the level of the electric pulses is generally proportional to the energy of the absorbed X-ray photon. As a result, spectral or energy-resolving information can be extracted by comparing the level of the electric pulse with an energy threshold value. The incident photons in the corresponding energy range above an energy threshold in each individual detector element of the X-ray detector are counted via comparison with a plurality of reference signals or the underlying energy threshold value.

During a method for energy calibration, these reference signals or these energy threshold values are usually set globally by the specification of a single digital value (DAC value) for each energy threshold for the entire X-ray detector. Each detector element can comprise a plurality of individually settable energy thresholds each with its own energy threshold value. The energy threshold values can be set at least partially the same or at least partially different for all detector elements, in particular after energy calibration. Alternatively, it is also possible to use indirect-conversion energy-resolving X-ray detectors, for example so-called sandwich-X-ray detectors.

The spatial resolution of the X-ray detector is typically established by the so-called pixel and/or sensor design, i.e. the structuring of the converter element or evaluation unit into detector elements. For example, smaller detector elements enable spatial resolution to be increased during the development of the X-ray detector. Herein, spatial resolution is substantially defined by the structuring of the converter element or of the evaluation unit into a matrix comprising a plurality of detector elements. The flat size of the detector elements also influences other properties of the detector element. For example, smaller detector elements generally result in higher pixel noise. A further possible drawback of smaller detector elements is lower frame rates, for example caused by bandwidth limitations in the case of larger matrices with a plurality of detector elements. Due to the high data volumes, therefore, the data of the detector elements can be read out less frequently.

The spatial resolution of an X-ray detector is described by its MTF (modulation transfer function). For known energy-integrating X-ray detectors, this variable is defined and is established by the pixel and sensor design. Influential parameters with respect to spatial resolution are inter alia the size of the detector elements, the sensitivity, size and shape of the diode or the sensitivity of the converter material and thickness of the sensor or converter material, for example CsI, CdTe or Se. This applies to both direct-conversion and indirect-conversion X-ray detectors.

SUMMARY

The inventors have recognized that, for many clinical applications, it would be desirable to be able to influence the MTF or spatial resolution retrospectively, i.e. after the recording of the data, for example in order to identify more details in fine structures, such as stents.

Embodiments of the invention disclose a method, an image-generating unit, a computer program product, a computer-readable medium and a medical device that enable the spatial resolution to be changed, in particular improved, after the recording of the data.

p

Embodiments of the invention are directed to a method, an image-generating unit, a computer program product, a computer-readable medium and a medical device.

An embodiment of the invention relates to a method for generating a mixed image data record based on energy-resolved recording via an energy-resolving X-ray detector comprising generating and mixing. In the generating, the first image value of a first image element of a first image data record is generated in a first energy range and the second image value of the first image element of a second image data record is generated in a second energy range. In the mixing, the first image value and the second image value are mixed in dependence on an image parameter and thereby the mixed image data record generated with a mixed image value of the first image element.

An embodiment of the invention further relates to an image-generating unit. The image-generating unit comprises a generating unit for generating the first image data record and the second image data record, a mixing unit for mixing the first image values and the second image values in dependence on an image parameter and for thereby generating the mixed image data record with a mixed image value of the first image element. The image-generating unit can further comprise a filter unit for filtering the first image data record and/or the second image data record by way of a filter function. The image-generating unit can further comprise a determining unit for the determining, wherein the image parameter is determined at least based on at least one subregion of the first image data record and/or of the second image data record. The image-generating unit can further comprise an optimization unit for the optimization of the filter function based on a type of examination.

Advantageously, the image-generating unit can carry out all the steps of the method according to an embodiment of the invention. In an alternative embodiment, the image-generating unit can be a distributed system.

An embodiment of the invention further relates to a computer program product with a computer program, which can be loaded directly into a storage facility of a control facility of a medical device, with program segments for carrying out all the steps of the method according to an embodiment of the invention when the computer program is executed in the control facility of the medical device. An embodiment of the invention further relates to a computer-readable medium on which program segments that can be read and executed by a computing unit are stored in order to carry out all the steps of the method according to an embodiment of the invention when the program segments are executed by the computing unit.

An embodiment of the invention further relates to a medical device comprising an image-generating unit according to an embodiment of the invention. The advantages of the method according to an embodiment of the invention can advantageously be transferred to the medical device. The medical device can be a radiography, fluoroscopy, mammography or computed tomography system.

An embodiment of the invention further relates to a method for generating a mixed image data record based on energy-resolved recording via an energy-resolving X-ray detector, comprising:

generating a first image value of a first image element of a first image data record in a first energy range and generating a second image value of the first image element of a second image data record in a second energy range; and mixing the first image value generated and the second image value generated in dependence on an image parameter, to generate the mixed image data record with a mixed image value of the first image element.

An embodiment of the invention further relates to an image-generating unit for generating a mixed image data record based on energy-resolved recording via an energy-resolving X-ray detector, comprising:

a generator to generate a first image value of a first image element of a first image data record in a first energy range and to generate a second image value of the first image element of a second image data record in a second energy range; and a mixer to mix the first image value and the second image value in dependence on an image parameter, to generate the mixed image data record with a mixed image value of the first image element.

An embodiment of the invention further relates to a storage facility of a control facility of a medical device, storing a computer program including program segments for carrying out the method of an embodiment when the computer program is executed in the control facility of the medical device.

An embodiment of the invention further relates to a non-transitory computer-readable medium storing program segments, readable and executable by an image-generating unit to carry out the method of an embodiment when the program segments are executed by the image-generating unit.

BRIEF DESCRIPTION OF THE DRAWINGS

The following explains example embodiments of the invention in more detail with reference to drawings, which show.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

An embodiment of the invention relates to a method for generating a mixed image data record based on energy-resolved recording via an energy-resolving X-ray detector comprising generating and mixing. In the generating, the first image value of a first image element of a first image data record is generated in a first energy range and the second image value of the first image element of a second image data record is generated in a second energy range. In the mixing, the first image value and the second image value are mixed in dependence on an image parameter and thereby the mixed image data record generated with a mixed image value of the first image element.

The energy-resolving X-ray detector can in particular be embodied as a counting X-ray detector, preferably with a direct-conversion converter element. Instead of an X-ray detector, it is possible to use a radiation or particle detector. The radiation or particle detector can be used as an X-ray detector. The energy-resolving X-ray detector can be embodied as a sandwich detector, for example comprising at least two converter layers in the converter element. The converter layers can be embodied for direct or indirect conversion. The X-ray detector can comprise a plurality of detector elements. An image data record can be generated from the detector element's measured values. The image data record includes image values. With two-dimensional X-ray recording, in the simplest case, the image value can, for example, substantially correspond to the X-ray detector's measured value. In the case of three-dimensional X-ray recording, a slice image can be reconstructed from several recordings and their measured values, wherein the slice image can form the image data record.

In an embodiment, in the generating, a plurality of image values are generated for the first image element. The first image value and the second image value include the image information for a substantially identical location in the image, but in different energy ranges. The first and the second energy range can be limited by way of at least one energy threshold value. The first energy range can, for example, be limited to higher energy values by way of a first energy threshold. A lower energy threshold can be defined above the noise limit and limit the first energy range to lower energy values. In the first measuring range, measured values with energy values between the lower energy threshold and the first energy threshold can be registered. In the second energy range, measured values with energy values above the first energy threshold can be registered. The discrimination of the energy ranges can be unilateral or bilateral.

The image parameter can be assigned to the first image element or a plurality of image elements of the X-ray detector. The image parameter can be assigned to first energy range and/or the second energy range. The method according to an embodiment of the invention can be expanded to more than two energy ranges. The method according to an embodiment of the invention can be performed for a plurality of image elements simultaneously or in succession. The steps of the method according to an embodiment of the invention can be repeated for a second image element.

The spatial resolution of a (quantum-)counting X-ray detector with small detector elements can be heavily dependent on the energy threshold value set. In the case of a very low energy threshold value, incident photons just outside the detector element can still result in a counted event or a measured value. The effective aperture of the detector element can hence be greater than the geometric aperture of the detector element. Hence, the effective aperture of the image element can also be greater than the geometric aperture of the image element.

If, on the other hand, the energy threshold value is set higher, for example only just below the energy of the X-ray photons, only events that strike the detector elements close to the center of the detector element can be counted since, on account of the size of the charge cloud, generally the total energy can only be deposited in the detector element for the centrally incident X-ray photons. In this case, therefore, the effective aperture can be smaller than the geometric aperture.

(Quantum-)counting X-ray detectors typically evaluate a plurality of energy thresholds simultaneously. The inventors have recognized that this results in an image data record with higher spatial resolution being available retrospectively. Since, however, the quantum efficiency of an energy-resolving, in particular counting, X-ray detector can be lower at higher energy threshold values, increasing the energy threshold value can have the result that the signal-to-noise ratio is reduced in regions of the image data record, in particular the image, with only few registered events.

Therefore, in an embodiment the inventors propose a method in which the image data records of the different energy ranges can be mixed locally, for example in dependence on the signal and the movement in the image as image parameters. In the case of a high signal or numerous events and/or little movement in the image or between different recordings, more information from the higher energy range or a plurality of higher energy ranges can be mixed into the final image or the mixed image data record. Hence, the weighting of the location information from the image data record with a higher energy range can be increased. For example, linear weighting of the first image data record and of the second image data record is possible. For example, the image data records can be broken down into different image frequency ranges.

Before the mixing of the first and second image data record, filtering and/or adjustment, for example based on a look-up table, can be applied for optimization. For example, image algorithms that are already known, for example for the optimization or reconstruction of moving images, can be expanded and advantageously improved with the method according to an embodiment of the invention.

In addition, an evaluation of image data records in the different energy ranges also enables conclusions to be drawn regarding the localization of the primary interaction point of an X-ray photon or event within the detector element or the X-ray detector. The lower the energy threshold value of the energy range, the greater the distribution of the possible primary interaction points can be. Hence, it is possible, for example by way of a plurality of energy threshold values, for the registered signal to be broken down into different parts each with different probability distributions for the location of the primary interaction.

In an embodiment, the inventors propose that the mixing ratio be varied between the first image data record and the second image data record in particular locally, i.e. from image element to image element or from image region to image region. For example, the mixing ratio can be dependent on the image content or on an image parameter.

Advantageously, the higher spatial resolution of the image data record with the higher energy range can be used to improve the spatial resolution in the mixed image data record.

According to one embodiment of the invention, the method further comprises a determining step, wherein the image parameter is determined at least based on at least one subregion of the first image data record and/or the second image data record. A different image parameter, for example with respect to the value or nature of the image parameter, can be determined for different image elements. The subregion can include at least one image element. The subregion can in particular include a plurality of adjacent image elements. In the determining step, the image parameter can be determined based on the image value of the first image element or the image values of a plurality of image elements including the first image element of the first image data record and/or the image value of the first image element or the image values of a plurality of image elements including the first image element of the second image data record. Advantageously, the spatial resolution can be selectively improved.

According to one embodiment of the invention, the image parameter is based on an image property, a spatial-frequency-band property or a time-variable image property compared to a previous recording. The image property can be determined in the spatial domain or in the frequency domain. The image property can, for example, be a contrast property, an intensity property or information on the signal-to-noise ratio. The spatial-frequency-band property can include information on edges, for example between different materials in the examination object in the image (data record), or the modulation transfer function.

The time-variable image property can be determined from two first and/or second image data records recorded with a time offset to one another, i.e. an image sequence. For example, it is possible to calculate a difference in the image values between the first recording and the second recording for an image element of the first and/or second image data record so that, for example, it is possible to identify a movement in the examination object or in the image. Alternatively, external signals can be used as image parameters, for example an ECG signal or information from an optical camera recording. If an image parameter exceeds a suitable threshold value, the mixing ratio can be matched to the image property. Advantageously, the spatial resolution can be matched to the image property. Advantageously, the spatial resolution can be improved in subregions of the mixed image that are of particular diagnostic relevance.

According to one embodiment of the invention, the method further comprises filtering the first image data record and/or the second image data record by way of a filter function. The first and/or the second image data record can, for example, be transformed by way of a Fourier transform into the spatial frequency domain and filtered there. The step of filtering can be performed before or after a determining step.

The first and/or the second image data record can be filtered. For example, the filtering step can use the inverse of the MTF, noise reduction, for example by way of frequency band breakdown, or edge retention in the spatial domain, for example by way of gradients from the image data record of the lower energy range. Advantageously, the image quality or the visual impression of the mixed image data record can be improved.

According to one embodiment of the invention, the method further comprises a filter-function optimization step based on a type of examination. The filter function can be selected in dependence on the materials present in the examination object in the recording region, for example contrast agents such as iodine or tissue (in particular water) or bone (in particular calcium). Advantageously, the first and/or the second image data record can be matched to the medical issue in question. For example, the filter function can be optimized for a material, a type of examination, an examination region, an examination program or an X-ray spectrum. The material can, for example, be iodine or calcium. The material can be typical of an object in the examination object, for example a wire or a stent. The type of examination can, for example, be fluoroscopy, mammography or radiography. Advantageously, optimum noise suppression and contrast optimization can be achieved in the mixed image data record.

According to one embodiment of the invention, in at least the first image element, the mixed image data record comprises a mixed image value of the first image element and, in other image elements or in at least one other image element, the respective first image value or the respective second image value. The mixed image value corresponds to the image value in the mixed image mixed from the first image value and the second image value. When the method according to the invention is repeated for further image elements, it is possible, for example, for a subregion with mixed image values surrounded by first image values and/or second image values to be embodied in the mixed image. Like the first image data record and the second image data record, the mixed image data record can include a plurality of image elements. Advantageously, the image or the mixed image data record can be improved in a subregion, wherein the first or second image data are retained in the other subregion.

According to one embodiment of the invention, the mixing is performed on a detector element by detector element basis in the spatial domain. The image values of adjacent detector elements can, for example, be used in the determining, filtering and/or optimization steps. In the mixing step, preferably only the first and second image values of the first detector element are mixed. In the mixing step, it is possible to use a look-up table, linear weighting, a (non-linear) function, a gamma function or logarithm function to mix or weight the first image value and the second image value. The mixing or the underlying function thereof can be based on measurements, calculations or machine learning. Advantageously, it is possible to avoid intermixing of the image values from adjacent detector elements. Advantageously, the image information from the first detector element can be substantially retained.

An embodiment of the invention further relates to an image-generating unit comprising devices for carrying out, for example, aspects of at least one embodiment of the method according to the invention. The image-generating unit comprises a generating unit for generating the first image data record and the second image data record, a mixing unit for mixing the first image values and the second image values in dependence on an image parameter and for thereby generating the mixed image data record with a mixed image value of the first image element. The image-generating unit can further comprise a filter unit for filtering the first image data record and/or the second image data record by way of a filter function. The image-generating unit can further comprise a determining unit for the determining, wherein the image parameter is determined at least based on at least one subregion of the first image data record and/or of the second image data record. The image-generating unit can further comprise an optimization unit for the optimization of the filter function based on a type of examination.

Advantageously, the image-generating unit can carry out all the steps of the method according to an embodiment of the invention. In an alternative embodiment, the image-generating unit can be a distributed system.

An embodiment of the invention further relates to a computer program product with a computer program, which can be loaded directly into a storage facility of a control facility of a medical device, with program segments for carrying out all the steps of the method according to an embodiment of the invention when the computer program is executed in the control facility of the medical device. An embodiment of the invention further relates to a computer-readable medium on which program segments that can be read and executed by a computing unit are stored in order to carry out all the steps of the method according to an embodiment of the invention when the program segments are executed by the computing unit.

An embodiment of the invention further relates to a medical device comprising an image-generating unit according to an embodiment of the invention. The advantages of the method according to an embodiment of the invention can advantageously be transferred to the medical device. The medical device can be a radiography, fluoroscopy, mammography or computed tomography system.

Figure 1:
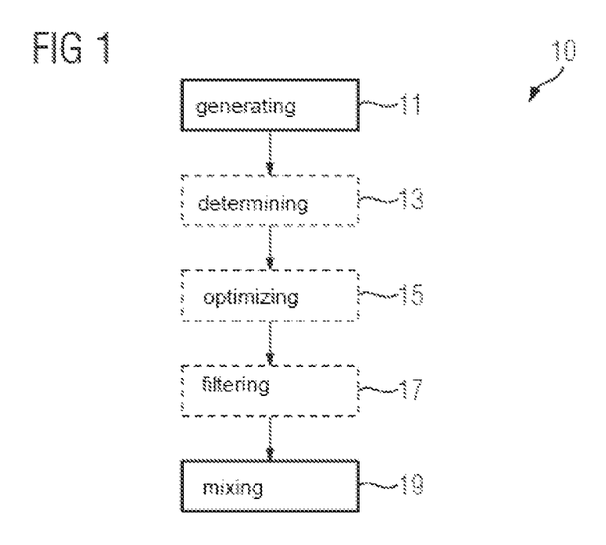
FIG. 1 a schematic representation of the method according to an embodiment of the invention.

FIG. 1 shows an example embodiment of the method according to the invention 10. The method 10 for generating a mixed image data record based on energy-resolved recording via an energy-resolving X-ray detector 25 comprises the steps of generating 11 and mixing 19. In the generating step 11, a first image value of a first image element of a first image data record is generated in a first energy range and a second image value of the first image element of a second image data record in a second energy range. In the mixing step 19, the first image value and the second image value are mixed in dependence on an image parameter thereby generating a mixed image data record with a mixed image value of the first image element. In at least the first image element, the mixed image data record comprises a mixed image value of the first image element. In other image elements, the mixed image can comprise the respective first image value or the respective second image value. The mixing 19 is performed on a detector element by detector element basis in the spatial domain.

The method 10 can further comprise a determining step 13, wherein the image parameter is determined at least based on at least one subregion of the first image data record and/or of the second image data record. The image parameter is based on an image property, a spatial-frequency-band property or a time-variable image property compared to a previous recording. The time-variable image property can be determined via external sensors.

The method 10 can further comprise a step of filtering 17 the first image data record and/or the second image data record by way of a filter function. The method 10 can further comprise a filter-function optimization step 15 based on a type of examination.

Figure 2:
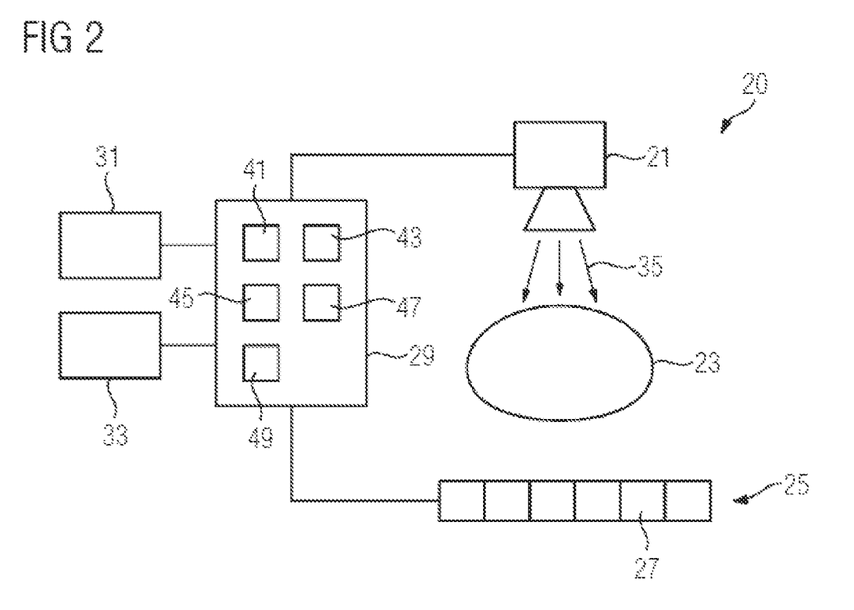
FIG. 2 a schematic representation of the medical device according to an embodiment of the invention.

FIG. 2 shows an example embodiment of the medical device according to the invention 20. The medical device 20 includes an X-ray source 21 and an energy-resolving X-ray detector 25 arranged opposite thereto. The X-ray source 21 emits X-rays 35. The examination object 23 is arranged between the X-ray source 21 and the X-ray detector 25. The X-ray detector 25 comprises a plurality of detector elements 27. An image value can be ascertained based on the measured value of the detector element 27. In the simplest case, the image value can substantially correspond to the measured value.

The medical device 20 further includes an image-generating unit 29. The image-generating unit 29 is connected to a display unit 31 and an input unit 33. The image-generating unit 29 includes a generating unit 41 for generating the first image data record and the second image data record and a mixing unit 43 for mixing the first image values and the second image values in dependence on an image parameter and thereby generating the mixed image data record with a mixed image value of the first image element. The image-generating unit 29 can further include a filter unit 45, a determining unit 47 and an optimization unit 49.

Although the invention has been described in greater detail by the preferred example embodiment, the invention is not restricted by the disclosed examples and other variations can be derived herefrom by the person skilled in the art without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for generating a mixed image data record based on energy-resolved recording via an energy-resolving X-ray detector, comprising:
    generating a first image value of a first image element of a first image data record in a first energy range and generating a second image value of the first image element of a second image data record in a second energy range, the first image value and the second image value corresponding to a same detector element in the X-ray detector;
    mixing only the first image value generated and only the second image value generated in dependence on an image parameter; and
    generating a mixed image data record with a mixed image value of the first image element.

2. The method of claim 1, further comprising:
    determining the image parameter at least based on at least one subregion of at least one of the first image data record and the second image data record.

3. The method of claim 1, wherein the image parameter is based on an image property, a spatial-frequency-band property or a time-variable image property compared to a previous recording.

4. The method of claim 1, further comprising:
filtering at least one of the first image data record and the second image data record using a filter function.

5. The method of claim 4, further comprising:
performing a filter-function optimization based on a type of examination.

6. The method of claim 1, wherein, in at least the first image element, the mixed image data record comprises a mixed image value of the first image element and, in at least other image elements, the mixed image data record comprises the first image value or the second image value.

7. The method of claim 1, wherein the mixing is performed on a detector element by detector element basis in a spatial domain.

8. An image-generating unit for generating a mixed image data record based on energy-resolved recording via an energy-resolving X-ray detector, comprising:
a generator to generate a first image value of a first image element of a first image data record in a first energy range and to generate a second image value of the first image element of a second image data record in a second energy range, the first image value and the second image value corresponding to a same detector element in the X-ray detector; and
a mixer to mix only the first image value and only the second image value in dependence on an image parameter, to generate the mixed image data record with a mixed image value of the first image element.

9. A storage facility of a control facility of a medical device, storing a computer program including program segments for carrying out the method of claim 1 when the computer program is executed in the control facility of the medical device.

10. A non-transitory computer-readable medium storing program segments, readable and executable by an image-generating unit to carry out the method of claim 1 when the program segments are executed by the image-generating unit.

11. A medical device comprising:
the image-generating unit of claim 8.

12. The method of claim 2, wherein the image parameter is based on an image property, a spatial-frequency-band property or a time-variable image property compared to a previous recording.

13. The method of claim 2, further comprising:
filtering at least one of the first image data record and the second image data record using a filter function.

14. The method of claim 13, further comprising:
performing a filter-function optimization based on a type of examination.

* * * * *